(12) United States Patent
Schmidt

(10) Patent No.: US 6,355,418 B1
(45) Date of Patent: Mar. 12, 2002

(54) CHIMERIC OLIGONUCLEOTIDES AND USES THEREOF IN THE IDENTIFICATION OF ANTISENSE BINDING SITES

(75) Inventor: Gunter Schmidt, Cambs (GB)

(73) Assignee: Xzillion GmbH & Co. KG, Frankfurt (DE)

( * ) Notice: Subject to any disclaimer, the term of this patent is extended or adjusted under 35 U.S.C. 154(b) by 0 days.

(21) Appl. No.: 09/043,149

(22) PCT Filed: Sep. 13, 1996

(86) PCT No.: PCT/GB96/02275

§ 371 Date: Mar. 13, 1998

§ 102(e) Date: Mar. 13, 1998

(87) PCT Pub. No.: WO97/10332

PCT Pub. Date: Mar. 20, 1997

(30) Foreign Application Priority Data

Sep. 14, 1995 (GB) .............................................. 9518864

(51) Int. Cl.⁷ ................................................ C12Q 1/68

(52) U.S. Cl. .......................................... 435/6; 536/24.5

(58) Field of Search .............................. 435/6; 536/26.5

(56) References Cited

U.S. PATENT DOCUMENTS 5,525,468 A * 6/1996 McSwiggen ................... 435/6

FOREIGN PATENT DOCUMENTS

| DE | 4424762 C1 | 7/1995 |
| WO | WO 89/05358 A1 | 6/1989 |

OTHER PUBLICATIONS

Ortigao et al., "Antisense Effect of Oligodeoxynucleotides with Inverted Terminal Internucleotidic Linkages: A Minimal Modification Protecting against Nucleolytic Degradation", *Antisense Research and Development*, 1992, pp. 129–146, vol. 2, Mary Ann Liebert, Inc., USA.

Giles et al., "Detection of Ribonuclease H–Generated mRNA Fragments In Human Leukemia Cells Following Reversible Membrane Permeabilization in the Presence of Antisense Oligodeoxynucleotides", *Antisense Research and Development*, 1995, pp. 23–31, vol. 5, Mary Ann Liebert, Inc., USA.

Mishra et al., In vitro selection of antisense obligonucleotides targeted to a hairpin structure, *Sciences De La Vie Life Sciences*, 1994, pp. 977–82, vol. 317, C.R. Acad. Sci. Paris, France.

Uchida et al., "Selection of antisense oligodeoxyribonucleotides that inhibit VEGF/VPF expression in a cell–free system", *Antisense Research and Development*, 1995, pp. 87–88, vol. 5, No. 1, Mary Ann Liebert, Inc., USA.

Uhlmann et al., "Antisense Oligonucleotides: A New Therapeutic Principle", *Chemical Reviews*, 1990, pp. 543–584, vol. 90, No. 4, American Chemical Society, Washington, D.C., USA.

Larrouy et al., "RNase H–mediated inhibition of translation by antisense oligodeoxyribonucleotides: use of backbone modification to improve specificity", *Gene*, 1992, pp. 189–194, vol. 121, Elsevier Science Publishers B.V., Belgium.

Cload et al., "Selection of Structure–Specific Inhibitors of the HIV Rev–Rev Response Element Complex", *J. Am. Chem. Soc.*, 1994, pp.437–442, vol. 116, The American Chemical Society, Washington, D.C., USA.

Giles et al., "Single base discrimination for ribonucleoase H–dependent antisense effects within intact human leukaemia cells", *Nucleic Acids Research*, 1995, pp. 954–961, vol. 26, No. 6, Oxford University Press, Oxford, UK.

Ho et al., "Potent antisense oligonucleotides to the human multidrug resistance–1 mRNA are rationally selected by mapping RNA–accessible sites with oligonucleotide libraries", 1996, pp. 1901–1907, vol. 24, No. 1, Oxford University Press, Oxford, UK.

Studier, "A strategy for high–volume sequencing of cosmid DNAs: Random and directed priming with a library of oligonucleotides", *Proc. Natl. Acad. Science*, 1989, pp. 6917–6921, vol. 86, The National Academy of Sciences, Washington, D.C. USA.

Hélène, "La strategie antisens: nouvelles approaches therapeutiques", *Synthèse*, 1994, pp. 253–73, vol. 10, John Libbey Eurotext, France.

* cited by examiner

*Primary Examiner*—Scott W. Houtteman
(74) *Attorney, Agent, or Firm*—Burns, Doane, Swecker & Mathis, L.L.P.

(57) ABSTRACT

A chimaeric oligonucleotide library for use in identifying an antisense binding site in a target mRNA, comprising a plurality of distinct chimaeric oligonucleotides capable of hybridizing to mRNA to form a duplex, the nucleotide sequences of which each have a common length of 7 to 20 bases and are generated randomly or generated from information characterizing the sequence of the target mRNA, wherein substantially all the nucleotide sequences of said common length which are present as sub-sequences in the target mRNA are present in the library, and wherein each nucleotide sequence comprises: a) a recognition region comprising a sequence of nucleotides which is recognizable by a duplex-cutting RNAase when hybridized to the mRNA, and b) a flanking region comprising a sequence of chemically-modified nucleotides which binds to the mRNA sufficiently tightly to stabilize the duplex for cutting of the mRNA in the duplex by the duplex-cutting RNAase, wherein the nucleotides constituting the flanking region are different from those constituting the recognition region, and wherein each oligonucleotide is protected against exonuclease attack.

19 Claims, 10 Drawing Sheets

Fig. 6A

Example ATG ———————— target TNFα mRNA ————————— AAAAA
                    ↑                    ↑
                   cut                  cut
                   site                 site 1. CAO$_S$    NNNNNnnnnnNNNNN  :(15-mer)

Yield 99.8% ATG ———————— TNFα mRNA ········——— AAAAA  full length mRNA
                                                (not cut)

0.15% ATG ——————  cut site 1  ········—AAAAA    cut species 1
              NNNNNnn    nnnNNNNN                (mRNA fragment)

0.05% ATG ——————  cut site 2  ········AAAAA     cut species 2
              NNNNnnn    nnNNNN                  (mRNA fragment)

2. RT-PCR synthesis of 1st cDNA strand:

ATG ———————————————— AAAAA ← mRNA
         ～～～～～～  TTTTT ← fragment
           cDNA              ← poly T primer
Denature (Heat/NaOH)

3.           cDNA
         ～～～～～～—TTTTT    1st cDNA strand
                +
   tailing of cut site: TdT and dCTP
                        or
                       (d dGTP)
                        ↓

CHIMERIC OLIGONUCLEOTIDES AND USES THEREOF IN THE IDENTIFICATION OF ANTISENSE BINDING SITES

FIELD OF THE INVENTION

The present invention relates to an oligonucleotide library, more particularly a chimaeric oligonucleotide library, and uses thereof in the identification of antisense binding sites in target mRNA and in providing potential therapeutic agents.

BACKGROUND TO THE INVENTION

Antisense oligonucleotides are single-stranded nucleic acids which are complementary to the coding or "sense" strand of genetic material. An antisense oligonucleotide is therefore also complementary to the mRNA produced from the genetic material. If antisense DNA or RNA is present in a cell with the mRNA, hybridisation takes place to form a duplex thereby preventing translation of the mRNA by ribosomes to make a protein. Thus, antisense RNA can be used to block the expression of genes that make proteins.

The antisense approach to the inhibition of gene expression, though conceptually straightforward, presents technologically demanding challenges. A variety of approaches have been taken by various academic groups and biotechnology companies. Oligonucleotides have been made with sugar modifications, such as 2'-O allyl ribonucleotides, and with backbone modifications in the phosphate group, such as phosphorothioate deoxyribonucleotides. However, production of these individual oligonucleotides for application as antisense therapeutics, reagents or tools for drug target validation has been hampered because methods of identifying potentially efficacious antisense compounds against a given target mRNA are extremely difficult. Even with an mRNA of known sequence, it is often impossible to predict what sub-sequences in the target mRNA might be available for antisense binding because of the three-dimensional structure of the mRNA and the association of RNA with proteins.

In an alternative approach to the use of chemically modified oligonucleotides, Lieber and Strauss (ref 22) report the use of a ribozyme expression library for the purpose of selecting cleavage sites in target RNAs. The ribozyme approach suffers from the disadvantage that it requires cleavage sites containing GUC or CUC and thus is not generally applicable to all possible cleavage sites. In addition, cleavage efficiency is relatively low, and chemical synthesis of ribozyme libraries is difficult.

SUMMARY OF THE INVENTION

According to one aspect, the present invention provides a chimaeric oligonucleotide library for use in identifying an antisense binding site in a target mRNA, which comprises a plurality of distinct chimaeric oligonucleotides capable of hybridizing to mRNA to form a duplex, the nucleotide sequences of which each have a common length of 7 to 20 bases and are generated randomly or generated from information characterising the sequence of the target mRNA, wherein substantially all the nucleotide sequences of said common length which are present as sub-sequences in the target mRNA are present in the library, and wherein each nucleotide sequence comprises:

a) a recognition region comprising a sequence of nucleotides which is recognisable by a duplex-cutting RNAase when hybridized to the mRNA, and b) a flanking region comprising a sequence of chemically-modified nucleotides which binds to the mRNA sufficiently tightly to stabilise the duplex for cutting of the mRNA in the duplex by the duplex-cutting RNAase, wherein the nucleotides constituting the flanking region are different from those constituting the recognition region; and wherein each oligonucleotide is protected against exonuclease attack.

The mRNA may be from human or other mammalian origin or from invertebrates. The term mRNA as used herein also encompasses the corresponding RNA from plants, viruses and bacteria.

Chimaeric Oligonucleotide

Each chimaeric oligonucleotide forming the library may be made synthetically using any commonly-available oligonucleotide sequence synthesizer. The exact length of the nucleotide sequence will reflect a balance between achieving the necessary specificity and keeping the length to a minimum to minimise cost. Preferably, the nucleotide sequence has a length in the range 10 to 20, more preferably 14 to 17 bases, yet more preferably around 15 bases.

The oligonucleotide is preferably protected against-nuclease attack so as to minimise degradation in the cell and increase its stability. This is particularly important in the design of an antisense compound for therapeutic use. Protection against exonuclease attack may be achieved by protecting one or preferably both ends of the oligonucleotide, for example by reverse T. or any other well-known method. Selection of the nucleotides constituting the recognition and flanking regions may also contribute to stability against nuclease because some nucleotides are more nuclease-resistant than others.

Preferably, each chimaeric oligonucleotide comprises two flanking regions, one on either side of the recognition region. In this way, the recognition region may be thought of as a "window" flanked by the two flanking regions so as to form with the mRNA a substrate for the duplex-cutting RNAase. In a preferred embodiment, each of the flanking regions is protected against exonuclease attack, preferably by reverse T. A preferred duplex-cutting RNAase is RNAase H, advantageously endogenous RNAase H (Ref 23).

The nucleotides constituting the recognition region are either modified or unmodified nucleotides and are preferably deoxyribonucleotides or phosphorothioate deoxyribonucleotides (see FIG. 4c). These nucleotides are recognisable by RNAase H when hybridized to mRNA. Typically, the recognition region comprises at least four nucleotides, preferably 5 to 10 nucleotides. In a particularly preferred embodiment, the recognition region comprises five nucleotides.

The nucleotides constituting the flanking region are chemically modified so as to increase the binding constant of the oligonucleotide for hybridization to the target mRNA and preferably to increase stability of the oligonucleotide in vivo. For a particular antisense oligonucleotide, the efficiency of hybridization to mRNA is a function of concentration. Thus, to improve hybridization as a given concentration, the stability of the hybrid duplex must be increased. A number of chemical modifications can be introduced into the oligonucleotide for this purpose and these fall into three broad classes (see also FIG. 1, regions 1, 2 and 3):

Sugar Modifications

Various modifications to the 2' position in the sugar moiety may be made. For example, both 2'-O methyl oligoribonucleotides and 2'-O allyl oligoribonucleotides may be useful (see references 1 and 2 and see also FIG. 2a and b). These analogues do not form hybrid duplexes with RNA which are substrates for RNAase H. In a particularly preferred embodiment of the present invention, two flanking regions, each having four or five of one of the modified sugar-containing oligoribonucleotides, flank a window region of four or five normal deoxyribonucleotides. The window region will thereby allow cleavage of the mRNA and the sugar-modified flanking regions increase the binding of the chimaeric oligonucleotide to the mRNA. Other 2' sugar modifications which may be used include F-substituted and $NH_2$-substituted oligoribonucleotides (see FIGS. 2c and 2d and references 3 and 4).

Base Modifications

The chemically-modified nucleotides constituting the flanking region may be modified in the base moiety. The propyne analogues of dT and dC, 5-propynyl deoxyuridine (see FIG. 3a) and 5-propynyl deoxycytidine (see FIG. 3b), both increase the duplex hybridization temperature and stabilize the duplex. This stabilization may be due to increased strength of hydrogen bonding to each Watson-Crick partner or increased base stacking (or both). 2-amino adenine is an analogue of dA (see FIG. 3c) and also increases the stability of the duplex. This may be due to the formation of a third hydrogen bond with thymine. The 2-amino adenine-thymine base pair is intermediate in stability between a G.C and a A.T base pair.

Phosphate Modifications

The chemically-modified nucleotides constituting the flanking region may be modified in the phosphate moiety. Under certain conditions such as low salt concentration, analogues such as methylphosphonates (FIG. 4a), triesters (FIG. 4b) and phosphoramidates (FIG. 4e) have been shown to increase duplex stability. The hybrid duplexes are not substrates for RNAase H. Further phosphate modifications include phosphorodithirates (FIG. 4d) and boranophosphates (FIG. 4f), each of which increase the stability of oligonucleotides.

Isosteric replacement of phosphorus by sulphur gives nuclease resistant oligonucleotides. (see reference 14). Replacement by carbon at either phosphorus or linking oxygen is also a further possibility (see FIG. 5).

In use, the chimaeric oligonucleotide of the invention acts as an antisense compound by specifically binding to target mRNA at an antisense binding site so that cleavage or cutting of the mRNA by a duplex-cutting RNAase takes place there. The chimaeric oligonucleotide will bind to the target mRNA to form a duplex. The recognition region is recognised by a duplex-cutting RNAase. The flanking region renders the duplex sufficiently stable to enable the RNAase to cut the mRNA in the duplex efficiently. Once cut, the mRNA and the oligonucleotide detach thereby leaving the oligonucleotide to bind a further mRNA. In this way, the chimaeric oligonucleotide acts catalytically.

Oligonucleotide Libraries

In a further aspect, the present invention provides use of an oligonucleotide library in a method of identifying an antisense binding site in a target mRNA, wherein the oligonucleotide library comprises a plurality of distinct nucleotide sequences, each having a common length in the range 7 to 20 bases, preferably 10 to 20 bases, and each of which comprises a substrate for a duplex-cutting RNAase if hybridised to the mRNA, which library is generated randomly, or generated from information characterising the sequence of the target mRNA, so that substantially all nucleotide sequences of said common length which are present as sub-sequences in the target mRNA are present in the library. The nucleotide sequences may comprise modified nucleotides, such as phosphorothioates, as described herein. The nucleotide sequences may be chimaeric or non-chimaeric.

In one embodiment, the library is generated randomly by means of an oligonucleotide sequence synthesizer. An aim of generating the sequences randomly is that substantially all possible nucleotide sequences of the specified length are generated. For a sequence of 10 bases in length (a 10-mer), $4^{10}$ distinct nucleotide sequences would need to be generated to cover all possibilities. This works out as approximately $10^6$ distinct nucleotide sequences. For a 15-mer, the library would need approximately $10^9$ to $10^{10}$ nucleotide sequences. Each nucleotide sequence will have a common length (i.e. they will all be 10-mers or will all be 11-mers, etc.). Any commonly-available oligonucleotide sequence synthesizer may be used for this purpose such as supplied by Applied Biosystems. All four possible bases are fed into the machine with an appropriate program using suitable nucleotides or modified nucleotides.

In an alternative embodiment, instead of generating the nucleotide sequences randomly they are generated from information characterising the sequence of the target mRNA. The sequence of the target mRNA needs to be known and can then be programmed into the oligonucleotide sequence synthesizer. For example, in the case of a gene which produces an mRNA of 450 nucleotides, a library of 15-mers would be produced with a total of 436 distinct nucleotide sequences (i.e. length of mRNA minus length of nucleotide sequence plus 1). In this way, all potential sub-sequences of the mRNA would be represented in the library. This is advantageous over the random generation of the library because there is no dilution of potentially useful nucleotide sequences by randomly generated sequences not present in the target mRNA. A further way of ensuring that all sub-sequences of the mRNA are present in the library is to produce, in the case of an mRNA of 450 nucleotides, a library of 30 15-mers (i.e. length of mRNA divided by the length of the nucleotide sequence).

In a further aspect, the present invention provides a method of identifying an antisense binding site in a target mRNA, which comprises:

1) incubating with the target mRNA an oligonucleotide library and a duplex-cutting RNAase under conditions to produce target mRNA cut at the antisense binding site; and 2) identifying the antisense binding site from the position of the cut in the mRNA; wherein the oligonucleotide library comprises a plurality of distinct nucleotide sequences, each having a common length in the range 7 to 20 bases, preferably 10 to 20 bases, and each of which comprises a substrate for the duplex cutting RNAase if hybridized to the mRNA; and wherein the oligonucleotide library is generated randomly, or generated from information characterising the sequence of the target mRNA, so that substantially all nucleotide sequences of such common length which are present as sub-sequences in the target mRNA are present in the library.

Use of an oligonucleotide library in this manner enables identification of one or more antisense binding sites in a target mRNA and such identification can be achieved very rapidly in comparison with known methods. No information about the three-dimension structure of the mRNA is required because the identification of the antisense binding sites is empirical. Incubation of the target mRNA with the oligonucleotide library and the duplex-cutting RNAase can, by suitable variation of the reaction conditions, produce target mRNA cut at one or more antisense binding sites. This is because the library will contain one or more oligonucleotides which are complementary to such binding sites and will bind thereto under appropriate conditions to form a duplex. The duplex acts as a substrate for the duplex cutting RNAase. When the mRNA is cut at the binding site the oligonucleotide is released and is thereby made available for further binding. The oligonucleotide therefore acts catalytically and the duplex-cutting RNAase acts enzymatically. The duplex-cutting RNAase is separate from the oligonucleotide library and is preferably from a cell extract. Preferably, the duplex-cutting RNAase is RNAase H. The target mRNA is also preferably from a cell extract. Advantageously, therefore, both RNAase H and mRNA are present in the same cell extract with which the oligonucleotide library is incubated.

The position of the cut in the mRNA may be determined by sequencing isolated cut target mRNA. Preferably, the cut target mRNA is amplified prior to isolation, for example by reverse transcription and polymerase chain reaction.

Once the antisense binding site is identified from the position of the cut in the mRNA and sequenced, an antisense oligonucleotide may be synthesized which is capable of binding to the site. In this way, a method is provided for the production of an antisense oligonucleotide. Thus, a chimaeric oligonucleotide of the type discussed above can be obtained. An important use of such a chimaeric oligonucleotide is as a therapeutic agent capable of hybridising to a specific antisense binding site in a target mRNA. The nucleotide sequence of the chimaeric oligonucleotide needs to be specific to the antisense binding site for this purpose.

In summary, using the library approach described herein, optimal sequences of effective antisense compounds can be identified against specific mRNA targets. The antisense compounds are useful as potential therapeutics, as tools for drug target validation, in diagnostics and as a research reagent.

The present invention will now be described in further detail, by way of example only, with reference to the accompanying drawings in which.

NUCLEOTIDE MODIFICATIONS

Figure 1:
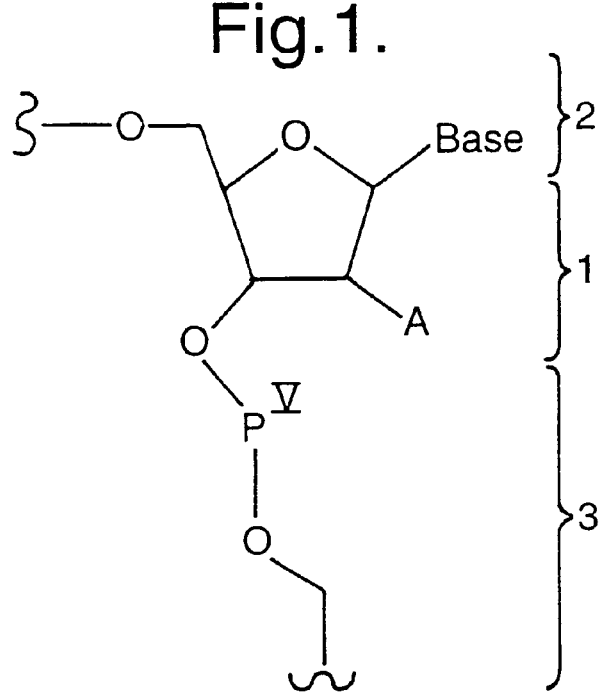
FIG. 1 shows a generalised structure for nucleotides.
Figure 2:
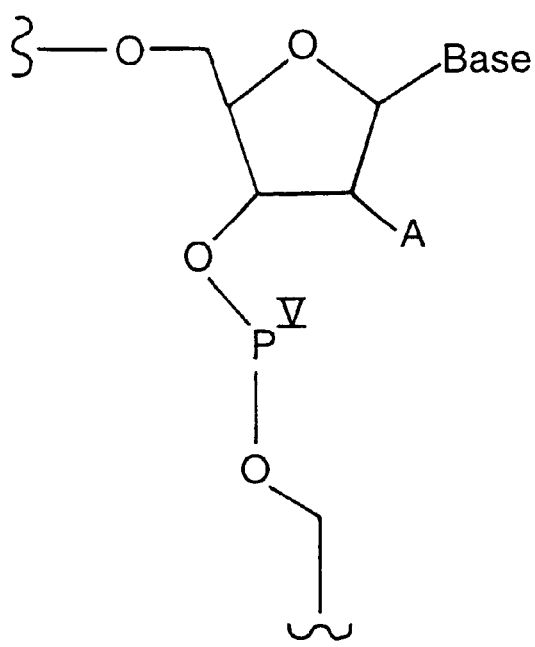
FIG. 2 shows a generalised structure for sugar moieties present in nucleotides.

FIG. 1 shows a generalised structure for nucleotides in which base 2 is connected to sugar 1 and phosphate 3 links the sugar to the next sugar in the sugar phosphate backbone. According to FIG. 2, substituent group A may be O-alkyl, aryl or alkaryl (in particular O—Me) (see Ref 1). Alternatively, substituent group A may be O-allyl (Ref 2), F (Ref 3), or $NH_2$ (Ref 4).

Figure 3:
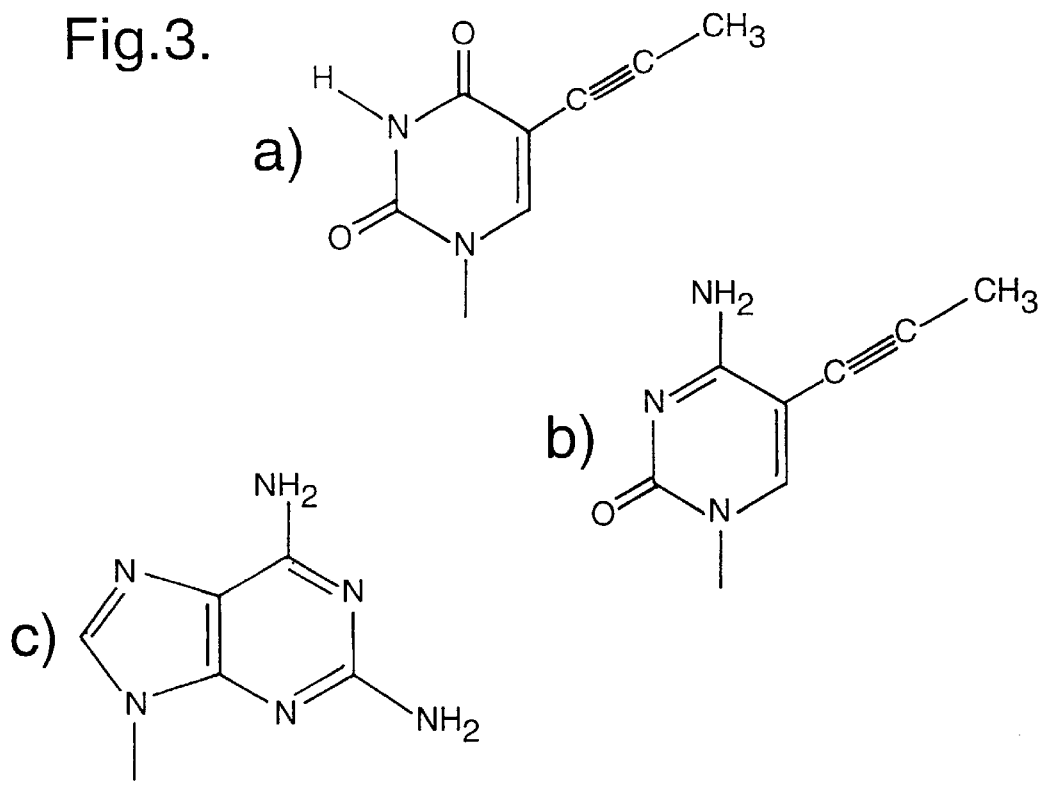
FIG. 3 shows generalised structures of modified base moieties in nucleotides.
Figure 4:
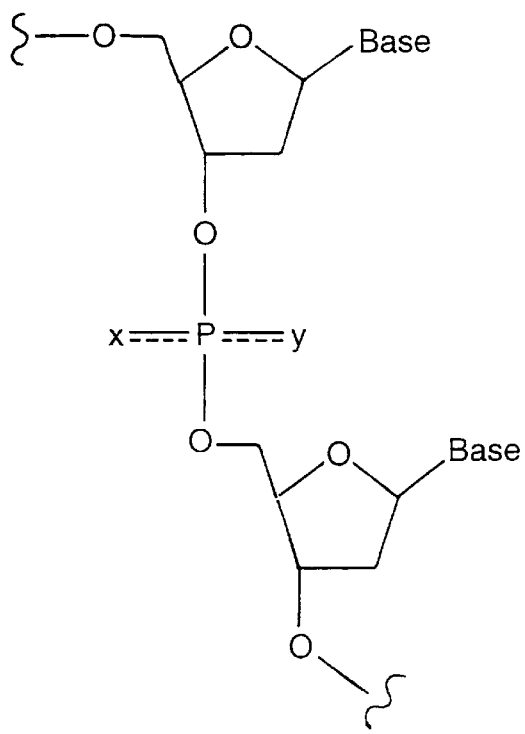
FIG. 4 shows generalised structures of modified phosphate moieties in oligonucleotides.

The bases shown in FIGS. 3a, 3b and 3c are discussed respectively in References 5, 6 and 7. Referring to FIG. 4, various phosphate modifications may be made, as summarised in the Table I below.

| x | y | Ref |
|---|---|-----|
| $CH_3$ | O | 8 |
| OR | O | 9 |
| S | O | 10 |
| S | S | 11 |
| NHR | O | 12 |
| $BH_3$ | O | 13 |

Figure 5:
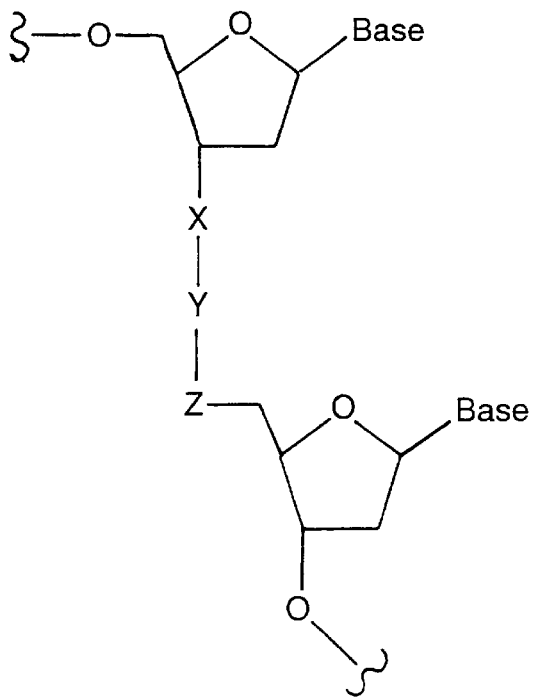
FIG. 5 shows isosteric modifications of the phosphate moieties in oligonucleotides.

Referring to FIG. 5, the phosphate moiety may be replaced in accordance with the following Table II

| x | y | z | Ref |
|---|---|---|-----|
| O | $CH_2$ | O | 15 |
| O | $CH_2$ | S | 16 |
| S | $CH_2$ | O | 17 |
| O | c=o | O | 18 |
| O | C=O | NH | 19 |
| $CH_2$ | NH | O | 20 |
| $CH_2$ | $NCH_3$ | O | } |
| $CH_2$ | O | $NCH_3$ | } 21 |

EXAMPLE 1

Figure 6B:
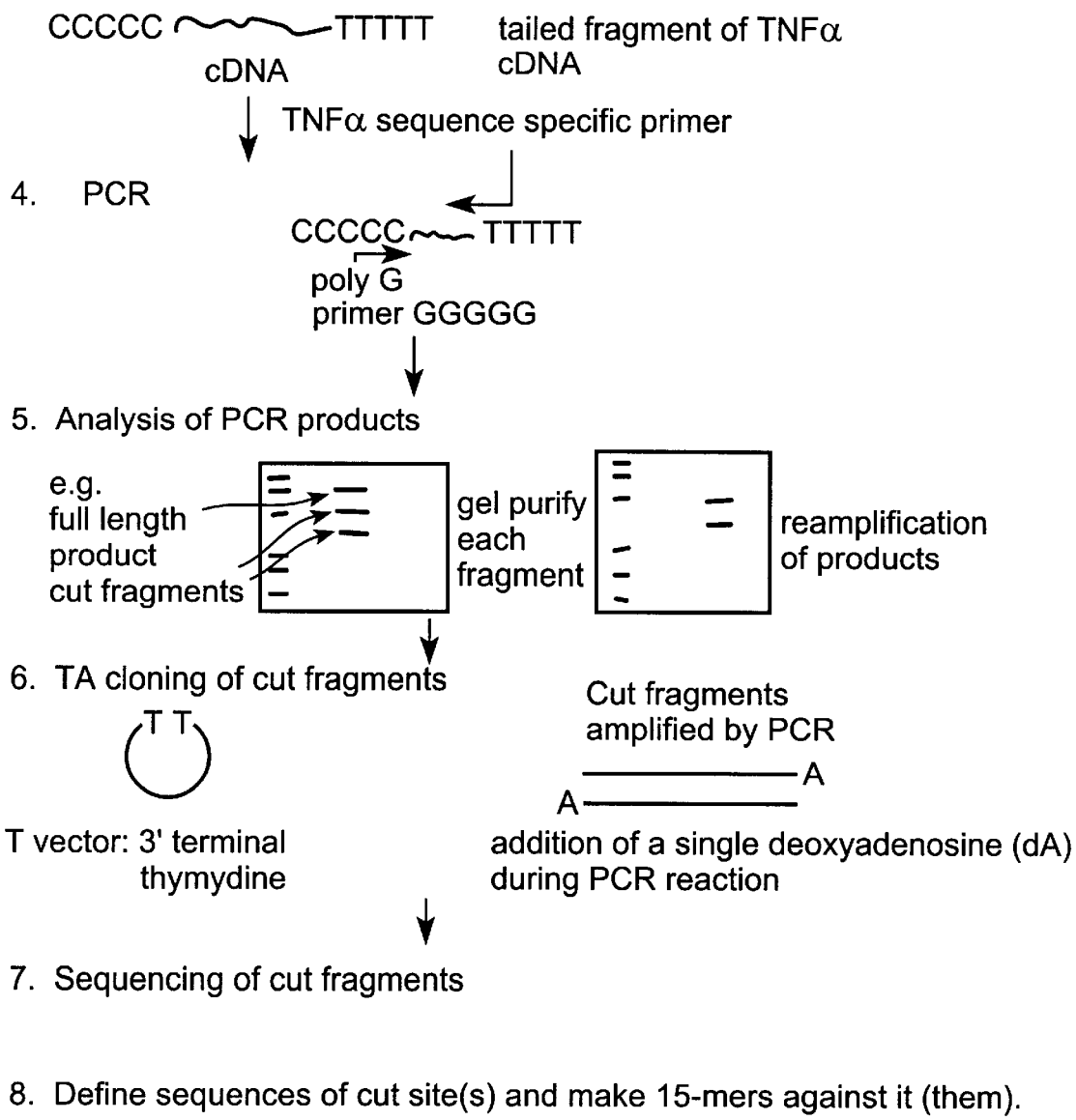
FIG. 6 shows a schematic representation of a method for identifying antisense binding sites from cut mRNA.

Referring to FIG. 6, the following illustrates a preferred method for identifying an antisense binding site in a target mRNA and for producing an antisense chimaeric oligonucleotide directed to that binding site (see also Ref. 22).

A chimaeric oligonucleotide library of the type described herein is incubated with an mRNA substrate. In this example, the target mRNA is TNF-α mRNA in a cellular extract. Incubation takes between one and three hours. As shown in step 1 of FIG. 6, two cut sites are produced at yields of 0.15% and 0.05% respectively. Most (99.8%) of the target mRNA is uncut. In this step, N and n each represent different nucleotides, as discussed above in the section on nucleotide chemistry. The library is either completely random (i.e. of the order of $10^9$ species) or specific to the target TNF-α (i.e. of the order of 1600 species).

According to step 2, a first cDNA strand is synthesized by using reverse transcriptase (RT). Oligo dT is used as a primer because the mRNA fragment has a poly A tail. Thermal denaturation under alkaline conditions yields a single strand of the first cDNA. According to step 3, the first strand cDNA is tailed with dC or dG to yield at least 10, usually 10 to 100 bases. All products (including both target mRNA and non-target mRNAs) now have a dT and a dC or dG tail.

In step 4, primers specific to the gene in question are designed to a region 5' of the poly A site. Using primers complementary to the gene and the dG (dC) tails, PCR is carried out to amplify full length target mRNA and cut target mRNA products.

In step 5, the PCR products are analysed by separation or polyacrylamide gel electrophoresis. In this way, cut products are separated from full length target mRNA by size. Cut products are identified as small bands and can be purified by gel purification. At this stage, cutting efficiency of the RNAase H can be measured by observing the intensity of the staining (e.g. on ethidium bromide stained agarose gels). Efficacy of the potential antisense drug depends upon cutting efficiency. Thus, at this stage, the dominant bands will identify products which have been cut most effectively by RNAase H and which may be efficaceous. It is these bands which are selected for cloning in a bacterial vector such as Bluescript.

According to step 6 of FIG. 6, TA cloning of cut fragments is effected using a T vector having a 3' terminal thimidine. Cut fragments are amplified by PCR and a single deoxyadenosine (dA) is added during the PCR reaction. In order to identify the specific recognition sequences of the effective compounds, the cloned cut RT PCR products are sequenced. The ends of the products are sequenced by dideoxysequencing and the specific sites should follow the poly G or poly C series produced in step 3. The partial sequence of each antisense binding site is thus identified in this manner and the complete sequence of the antisense binding site is deduced from a sequence data bank. The complete sequence information is used to synthesize a suitable oligonucleotide (for instance a further chimaeric oligonucleotide) which can then be tested for efficacy in a cell-based system with suitable controls. For example, to eliminate the possibility that non-antisense mechanisms are operating, the controls will consist of both randomized variants of the successful sequence or sequences containing the same residues and the corresponding sense sequences.

EXAMPLE 2

Identification of Oligonucleotides with Optimum Antisense Activity Against TNF α mRNA Chimaeric oligonucleotide libraries were incubated with a target mRNA, in this case that of the TNF α gene.

Experimental Methods

Construction of Antisense Oligonucleotide Libraries

To determine the optimal length of antisense oligonucleotides required for specific mRNA hybridisation, oligonucleotide libraries of 8 nt and 12 nt have been synthesised by Oswel DNA Services Ltd. The libraries comprise of:

Random nucleotide sequences comprising all possible combinations of sequences
Specific anti-mRNA sequences to:
  Series 1: the 5' untranslated cap region (nucleotides 1 to 96 of mRNA, see Appendix 1)
  Series 2: a stable stem loop region within the mRNA transcript (nucleotides 1225 to 1321 of mRNA, see Appendix 2)
  Series 3: the 3' untranslated region (nucleotides 1489 to 1585 of mRNA, see Appendix 3)

Production of in vitro Transcription Construct

TNFα plified from pE4 (a TNFa cDNA construct obtained from ATTC, American Type Culture Collection), using the following dUTP containing primers:

F 1 (Sense)
5'-CAUCAUCAUCAUUCUGCUCUAAAAGCUGCUG-3' (SEQ ID NO:1)
F 2 (Sense)
5'-CUACUACUACUACCUAAGCAACCUUUAUUUCUCG-3' (SEQ ID NO:2)

The dUTP tags provide both a means of directional cloning of the cDNA into the vector insertion pAMP1, and also play a crucial part in the cloning reactions themselves.

Optimal thermal cycling parameters were as follows:

| Temperature | No. of Cycles | Time |
|---|---|---|
| 96 C. | 1 | 2 mins |
| 94 C. | 25 | 30 secs |
| 53 C. | 1 | 30 secs |
| 72 C. | 1 | 90 secs |
| 72 C. | 1 | 10 mins |

The amplified cDNA product was purified using the Quiaquick PCR purification kit (Quiagen). Once purified, 50 ng of cDNA was cloned into pAMP1 using the CloneAmp pAMP1 system for rapid cloning of amplification products (GibcoBRL) to create the plasmid pTNF8 according to the manufacturers protocol. The sequence integrity of the construct was confirmed by sequences analysis.

An in vitro transcript template was prepared by linearisation of 50 μg pTNF8 by BamHI prior to transcription using the Ribomax large scale RNA production system—T7 RNA polymerase from Promega.

Unicorporated ribonucleotides and premature termination transcripts were removed by spin column chromatography (Chromspin-400 DEPC treated, Clontech) and analysed by formaldehyde gel electrophoresis (Sambrook et al, 1989).

Cleavage of mRNA Using Gene Specific Libraries

1) The following reaction was set up in a total volume of 100 μl:
    20 μM TNF a mRNA
    200 μM of each antisense TNF α oligonucleotide (12 nt or 8 nt of contiguous sequence)
    20 mM KCl
    10 mM $MgCl_2$
    20 mM Tris-HCl, pH 7.5
    0.1 mM EDTA
    0.1 mM DTT
2) The reaction was incubated at 37° C. for 5 minutes prior to the addition of 0.1 μg/μl of RNAse H.
3) The above was incubated at 37° C. for 40 minutes.
4) RNAse H activity was inhibited by phenol/chloroform extraction.
5) 20 ng glycogen was added to the reaction products.
6) Antisense oligonucleotide libraries were removed by spin column chromatography (Chromspin-30 DEPC treated, Clontech).
7) RNA was precipitated by the addition of 2.5 volumes (100 μl) ethanol, 0.1 vols. 3M sodium acetate at pH 5.2.
8) Pelleted RNA was washed with 70% ethanol, before resuspension in 16 μl of DEPC treated water.

Cleavage of mRNA Using Random Libraries

The reaction protocol was as above for the gene specific libraries but using 20 μM of the random library as supposed to 200 nM used above.

Primer Extension Analysis of mRNA Fragments

The oligonucleotide libraries were incubated with the in vitro transcribed TNFa mRNA and with RNAse H. To identify the sequences flanking the cut sites, the fragments generated in the incubation above were amplified by PCR using several primers targeted to various regions of the RNA thus ensuring that no combinations of cut fragments would be missed in the amplification steps.

Primer extension analysis experiments were performed, each using 2 pmol of one of the FAM-labeled primers listed below. This was used to prime the reverse transcription of 8 μl of the RNA cleavage products, generated by the protocols above, using the Superscript II RNAse H reverse transcriptase (GibcoRL) according to the manufacturers instructions. Primer extension reactions were performed in duplicate, as were RNAse H negative controls for each primer tested.

The cDNA fragments so formed were analysed upon a 4% acrylamide denaturing gel run in an ABI (Applied Biosystems Inc) 377 prism sequencing apparatus, and subsequent analysis using the GeneScan version 2.0 software.

Samples for the ABI 377 apparatus are fluorescently labelled, and gel separation is measured as the time taken for a band to reach a fluorescent detector which scans the gel at a specific point. The GeneScan software converts this time resolved data back to the usual format or can calculate sizes directly if fluorescently labelled size standards are present in the sample. Size standards will carry a different fluorescent marker to the samples.

Primers Used in Primer Extension Analysis

| Primer Code | Primer | Sequence | |
|---|---|---|---|
| F2 | | GATTCAGGAATGTGTGGCCT | (SEQ ID NO:3) |
| | 956: | GATTCAGGAATGTGTGGCCT CCTGG | GCACA:975 GCACA:975 (SEQ ID NO:4) |
| F3 | | CAACCTCCTCCTCTGCCATCAAG | (SEQ ID NO:5) |
| | 586: | CAACCTCCTCTCTGCCATCAAG AAGCT | (SEQ ID NO:6) AGCCC:607 |
| T8836 | | GTTCCTCAGCCTCTTCTCCTTC | (SEQ ID NO:7) |
| | 178: | GTTCCTCAGCCTCTTCTCCTTC TGCTT | (SEQ ID NO:8) CTGAT:199 |
| T8837 | | GAAAACGGAGGCTGAACAATAG | (SEQ ID NO:9) |
| | 1366: | GAAAACGGAGGCTGAACAATAG TCCGT | (SEQ ID NO:10) GCTGT:1387 |
| T8838 | | CTACTATTCAGTGGCCGAGAAA | (SEQ ID NO:11) |
| | 1544: CTAC- TAT- TCAGTGGCCGAGAAA TCGGC | (SEQ ID NO:12) TAAAG:1564 | |

Principle of Quantative RNA PCR

Having determined the cut sites, it would be advantageous to determine which of the corresponding ODNs mediate cleavage most efficiently. To this end a quantitative RT PCR assay has been developed.

The quantity of uncleaved mRNA is assayed by analysing separate overlapping regions of the target mRNA using PCR reactions such that the whole mRNA is covered by the overlapping regions. With this approach the worker does not need to know the binding site of the antisense ODN and therefore this method is ideal for use in the random library approach as well as for targeted antisense ODNs. Copies of the sequences corresponding to the overlapping regions that have been chosen are generated, with a reasonably sized specific internal deletion, e.g. about 50 bp, removed, such that they can be cloned to allow in vitro transcription of the deletion fragments. These deletion fragments can then be used as an internal standard RNA control for quantitative RT PCR.

A known amount of one of the standards is added to the RNA sample to be assayed. Following reverse transcription of this mixture, using a gene specific primer, PCR is carried out using fluorescently labeled primers and the reaction is run on an ABI 377 prism sequencing apparatus and the peaks corresponding to the amount of each product, is determined. Since the starting quantity of the standard is known, the amount of other products can be deduced by calibrating the intensity of the fluorescence of the products against that of the standard.

Producing an internal standard like this overcomes many of the problems associated with quantitative RT PCR. Firstly, it acts to control for varying efficiencies between individual RT reactions and secondly, as the standard and the PCR target have the same primer sequence, and the same internal sequence ( apart from the internal deletion of the control) they will behave in a PCR reaction in the same way and should thus amplify with equal efficiency when the PCR reaction is stopped in the log phase.

Methodology of Quantitative RNA PCR

The TNFα mRNA was divided into three overlapping PCR fragments for analysis, these being fragment A (bases 14–557), fragment B (bases 502–1062) and fragment C (bases 1035–1575).

Primer sequences:
  A forward GCTGCCAGGCACIGTTCTCTTCC (SEQ ID NO:13) reverse CTGATGGTGTGTGGGTGAG-GAGC (SEQ ID NO:14)
  B forward CTTCAAGGGCCAAGGCTGCCC (SEQ ID NO:15) reverse GCTCCCTGGTCTCCAGATTCC (SEQ ID NO:16)
  C forward GCCTACAGCTTTGATCCCTG (SEQ ID NO:17) reverse GCAACCTTTATTTCTAGCCACTG (SEQ ID NO:18)
(all forward primers are labelled with a 5' FAM fluorescent moiety)

1. Production of Internal Competitive RNA Standards

In order to obtain fragments A,B and C with a 50 bp deletion (approx), for use as internal competitive RNA standards, 'deletion primers' were produced. These primers have the appropriate forward sequence (either A, B or C) followed by 20 bp (approx.) of sequence 50 bp (approx.) 3' to the forward sequence. When PCR is performed with deletion primers and the appropriate reverse primers the fragments generated are effectively the A,B or C fragments with a 50 bp (approx.) deletion 3' to the forward primer.

Fragment A deletion forward primer
  G C T G C C A G G C A G G T T C T C T T C C G C A C T-GAAAGCATGATCCGGG (SEQ ID NO:19)
Fragment B deletion forward primer
  C T T C A A G G G C C A A G G C T G C C C C A A G G T-CAACCTCCTCTCTGC (SEQ ID NO:20)
Fragment C deletion forward primer
  G C C T A C A G C T T T G A T C C C T G G G A C T-TGAGCCGACCTCACC (SEQ ID NO:21)

1.1 PCR reactions were performed on a Perkin Elmer 9600 PCR machine using Perkin Elmer Amplitaq polymerase (1 unit) with the manufactures buffer with 30 pmole of each of the appropriate forward deletion primer and reverse primer; 1.5 mM MgCl2; 10 mM dNTP's; 10 ng of pTNF8 TNFα clone. Cycling times were 1 cycle of 95° C. 5 min followed by 35 cycles of 95° C. for 30 sec, 48° C. for 1 min, 72° C. for 2 min with a single final cycle of 72° C. for 10 min.

1.2 PCR products were separated on a 2% agarose gel. Bands were excised and purified with the Qiagen QIAquick Gel Extraction Kit according to the manufactures protocol. Purified bands were cloned into the pCR 2.1 vector (Invitrogen) using the TA Cloning Kit (Invitrogen) according to the manufactures protocol. Sequence and orientation of the inserts was checked by sequencing using standard methods.

1.3 Clones which yield RNA with the same sense as TNF α mRNA, when transcribed from the T7 RNA polymerse site in pCR2.1, were selected. RNA for each deletion fragment was transcribed from the appropriate clones using the RiboMAX RNA Production System with T7 RNA polymerase (Promega) according to manufactures instructions. The transcribed RNA was then purified on a Sephacryl S-500 HR gel filtration column (Pharmacia) using a DEPC treated 25 mM Tris-HCl, 150 mM NaCl, 24 mM MgCl2 pH7.4 buffer under gravity flow at 4° C. RNA was eluted from the column at 110–130 ml of flow through and was precipitated using 2.5 volumes of 100% ethanol and resuspended in 100 uL distilled water.

The RNA TNFα deletions (internal competitive RNA standards) will now be referred to as AD (for the A fragment deletion), BD (for the B fragment deletion) and CD (for the C fragment deletion).

2. Quantification of Cleaved TNFα mRNA by Competitive RNA PCR

To describe this methodology a specific example is used:

An antisense cleavage experiment is performed using an anti sense oligo which cleaves within the C fragment. This cleaved RNA will from now on be referred to as X.

2.1 Six EZ rTth RNA PCR (Perkin Elmer) reactions are set up according to the manufactures instructions each containing 0.05 ng of X with primers for fragment C (numbered C1–C6) and six identical reactions with primers for fragment B (numbered B1–B6). A serial dilution of CD is then added to C1–6, ie 50 ng of CD to (1; 5 ng of CD to C2; 0.5 ng of CD to C3; 0.05 ng of CD to C4; 0.005 ng of CD to C5; 0.0005 ng of CD to C6. A corresponding serial dilution of BD is also added to B1–6.

2.2 The RNA PCR reaction is then performed on a Perkin Elmer 9600 PCR machine using the following cycles. 1 cycle of 94° C. for 0 sec; 48° O for 0 sec; ramp to 65° C. over 5 min and hold for 35 min, 1 cycle of 95° C. for 1 min, 32 cycles* of 95° C. for 25 sec; 65° C. for 1 min. 1 cycle 65° C. for 7 min.

(*32 cycles are used so that the reaction stops while still in log phase)

2.3 The reactions are then run on an ABT 377 and the peak hights of the C/B fragments and CD/BD fragments collected for each sample.

Figure 7A:
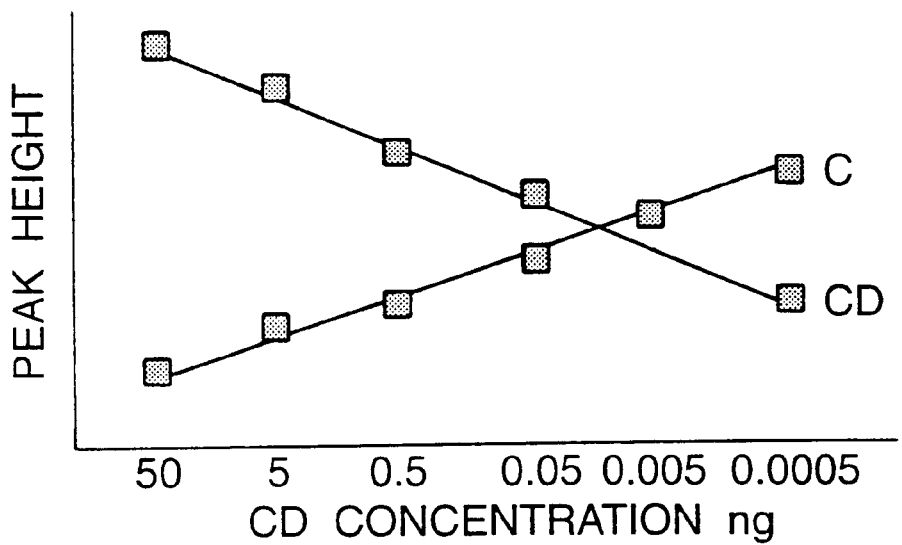
FIGS. 7a and 7b show calibration graphs of fluorescence against amounts of standard and sample oligonucleotides.
Figure 7B:
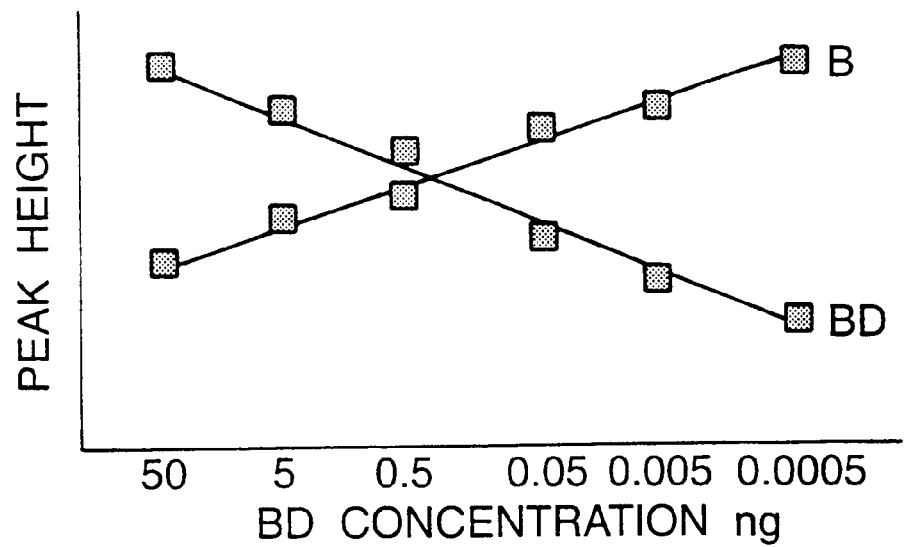

2.4 A graph is then plotted of CD concentration against C and CD peak height (see FIG. 7a), and similar FIG. 7b plotted for the B reactions. The point at which the two lines cross refers to the point at which the concentration of CD RNA is equimolar to the concentration of available C fragment RNA. As the antisense oligo cleaves within fragment C the concentration of available C RNA will be lower than the concentration obtained at the cross over point from the B reaction graph.

Hence, by comparing this two figures it is possible to quantify the cleavage of TNFα by the antisense oligo.

Results

Primer Extenstion of Fragments from Series 1 of 12 nt Gene Specific Oligonucleotides The primer used for primer extension experiments was T8836.

Figure 8:
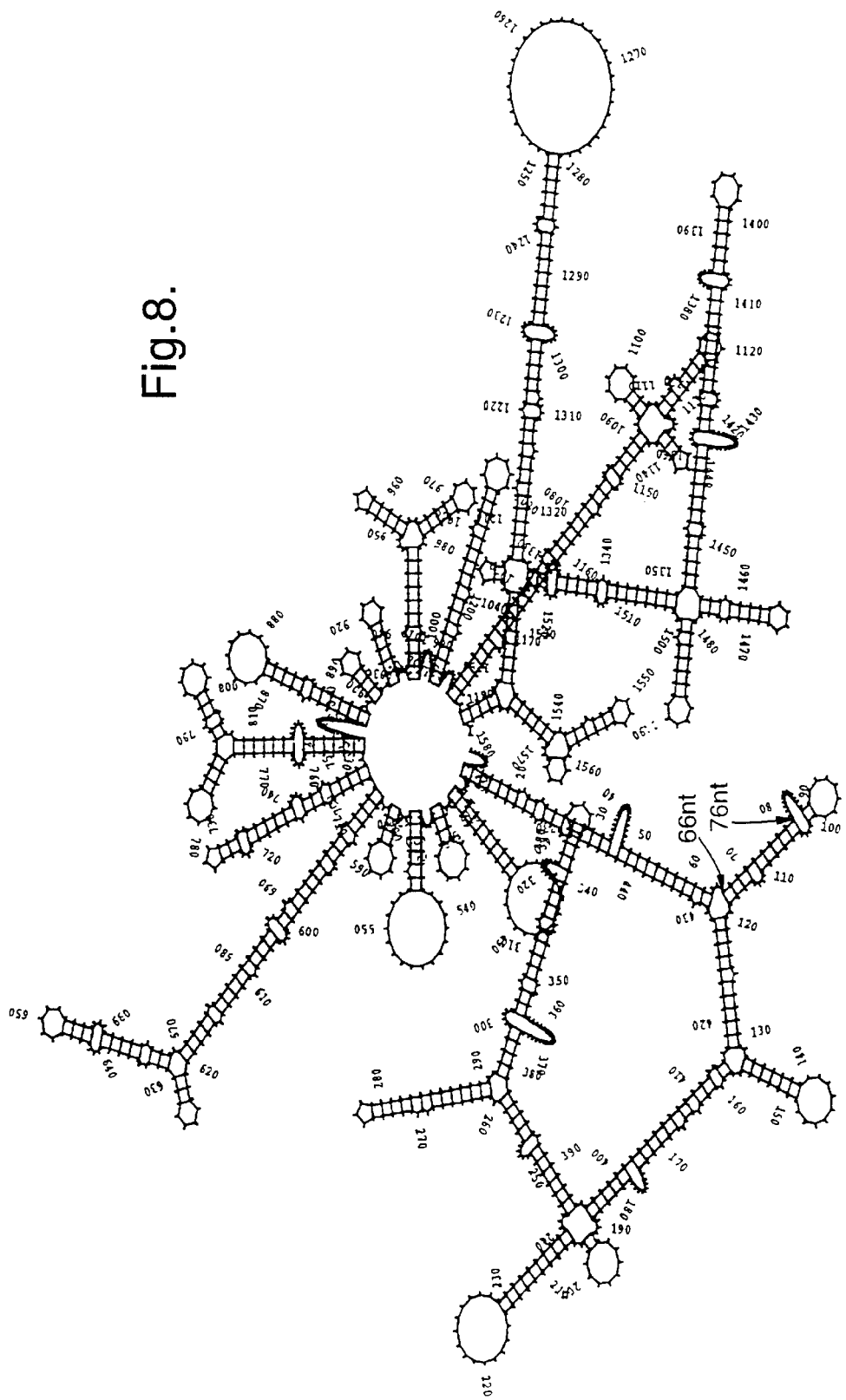
FIGS. 8 to 12 show computer predictions of the secondary structure of TNF-α mRNA and their cut sites.

Fragments of 124 nt and 134 nt were detected. These correspond to antisense cut sites in the mRNA at nucleotides 76 and 66. (See FIG. 8)

Cleavage Site 76 Corresponds to Antisense Oligonucleotide GTGTCCTTTCCA (SEQ ID NO:22)

Cleavage Site 66 Corresponds to Antisense Oligonucleotide GGGGAGAGAGGG (SEQ ID NO:23)

Primer Extenstion of Fragments from Series 1 of 8 nt Gene Specific Oligonucleotides The primer used for primer extension experiments was T8836.

Figure 9:
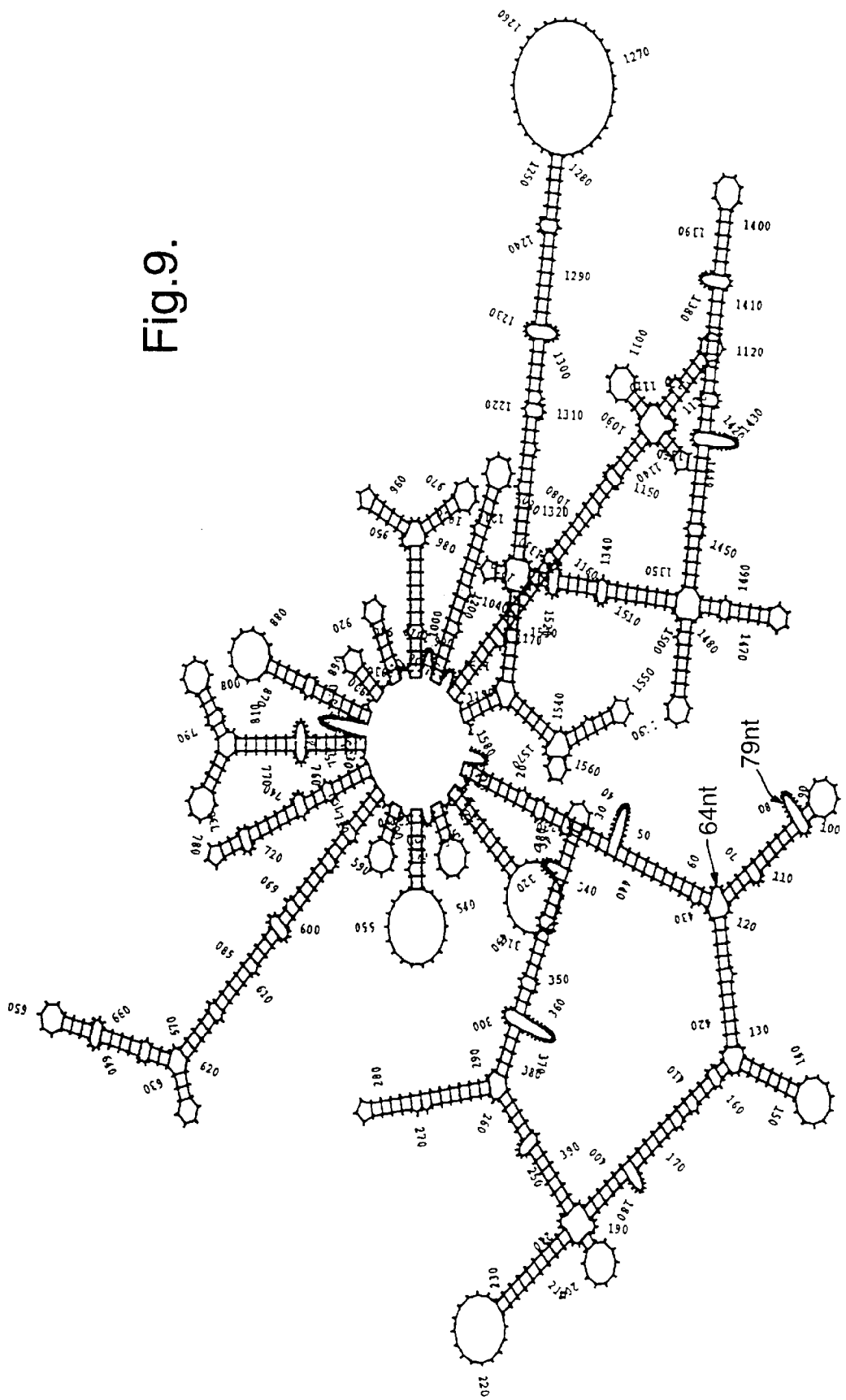

Fragments of 121 nt and 136 nt were detected. These correspond to antisense cut sites in the mRNA at nucleotides 79 and 64. (See FIG. 9)

Cleavage Site 79 Corresponds to Antisense Oligonucleotide CCTTTCCA

Cleavage Site 64 Corresponds to Antisense Oligonucleotide GGGGAGAG

Primer Extenstion of Fragments from Series 2 of 12 nt Gene Specific Oligonucleotides The primer used for primer extension experiments was T8838.

Figure 10:
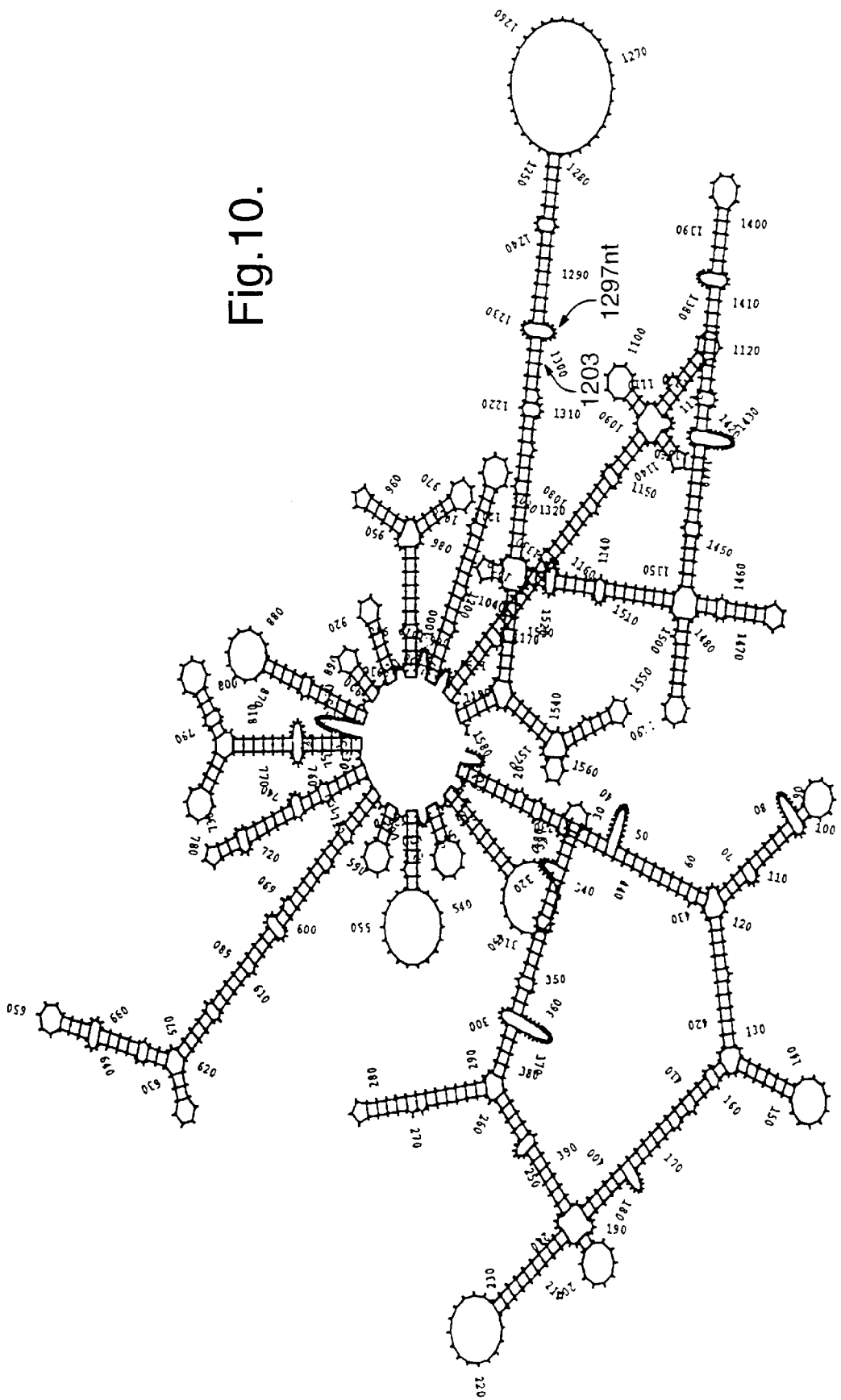

Major fragments of 261 nt, 265 nt and 275 nt were detected. These correspond to antisense cut sites in the mRNA at nucleotides 1289, 1297 and 1303. (See FIG. 10) Some minor peaks were detected in earlier experiments, under slightly differing conditions, corresponding to fragments at 281 and 282 nt.

Cleavage Site 1303 Corresponds to Antisense Oligonucleotide
GGTCTCCCAAAT (SEQ ID NO:24)

Cleavage Site 1297 Corresponds to Antisense Oligonucleotide
AAATACATTCAT (SEQ ID NO:25)

Primer Extenstion of Fragments from Series 2 of 8 nt Gene Specific Oligonucleotides The primer used for primer extension experiments was T8838.

Figure 11:
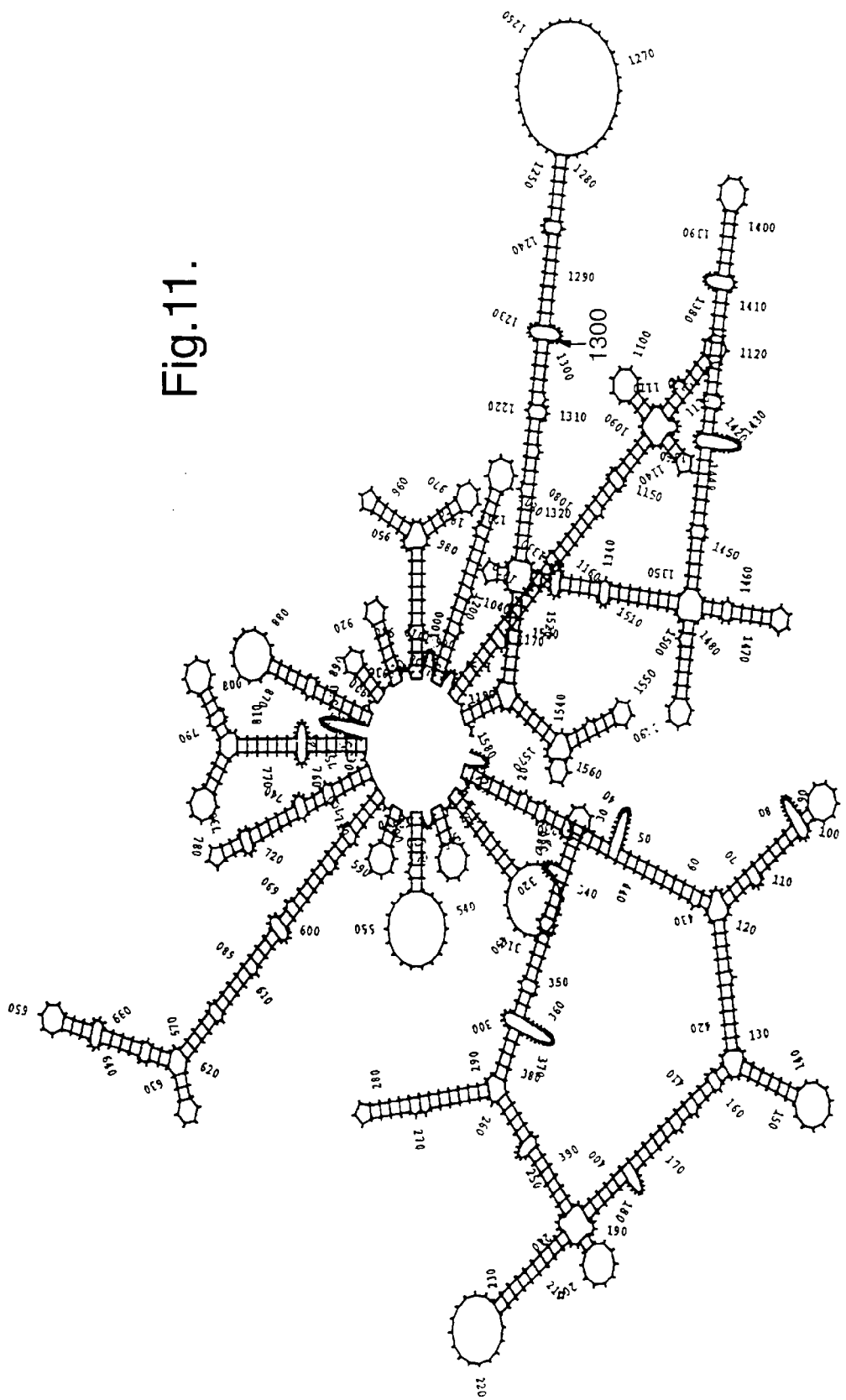
Figure 12:
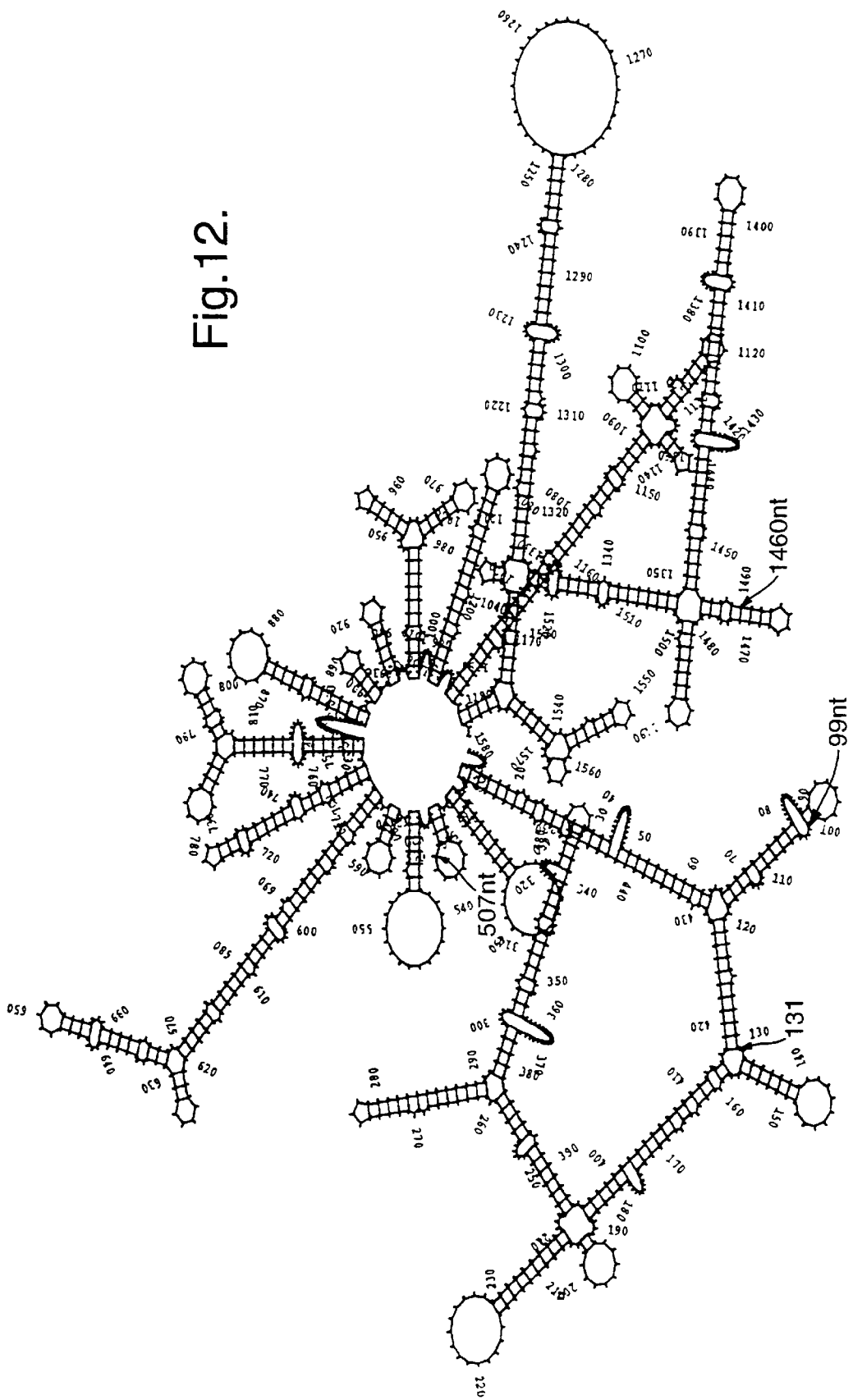

The major fragment was detected at 264 nt. These correspond to antisense cut sites in the mRNA at nucleotides 1300. (See FIG. 11)

Cleavage Site 1300 Corresponds to Antisense Oligonucleotide
TCCCAAAT

Primer Extenstion of Fragments from Series 3 of 12 nt Gene Specific Oligonucleotides The primer used for primer extension experiments was T8838.

Unfortunately, no reliable data was acquired from these experiments or for series 38 mer libraries.

Primer Extenstion of Fragments from Rrandom 12 nt Oligonucleotides

All five of the primers, listed in the method, were used in these primer extension experiments:

| Primer | Fragment Lengths | Cut Sites |
|---|---|---|
| F2 | 112 | 863 nt |
| F3 | 100 | 507 nt |
| T8836 | 69 | 131 nt |
| T8837 | None | None |
| T8838 | 104 | 1460 nt |

| Site of Site of mRNA cleavage | Predicted Antisense Sequence |
|---|---|
| 131 nt | GAGCGCCTCCTC (SEQ ID NO:26) |
| 507 nt | TGGCCCTTGAGA (SEQ ID NO:27) |
| 1460 nt | TAGACAACTTAA (SEQ ID NO:28) |

Results of Quantitative RNA PCR on Series 2 Oligonucleotides

The results of these experiments, under the conditions used, did not detect any difference in the cleavage efficiency of the oligonucleotides tested. The results suggested that all 5 cleaved with almost 100% efficiency.

| oligo | b peak height | bd peak height (@5 ng con) | amount to (5 × b peak height/bd peak height) | c peak height | cd peak height @5 ng con | amount c (5 × b peak height/cd peak height) |
|---|---|---|---|---|---|---|
| TCATCTGT | 130680 | 16906 | 38.6 | 75712 | 139347 | 2.7 |
| AAATACAT | 73597 | 42672 | 8.6 | 0 | 96686 | 0 |
| TCCCAAAT | 108621 | 34437 | 15.7 | 22336 | 1104770 | 1.06 |
| AAATACATTCAT | na | na | na | 49785 | 234045 | 1.06 |
| GGTCTCCCAAAT | 81504 | 51354 | 7.9 | 0 | 40134 | 0 |

Oligonucleotides tested:
  1283–90 TCATCTGT
  1291–98 AAATACAT
  1299–1306 TCCCAAAT
  1287–98 AAATACATTCAT (SEQ ID NO: 29)
  1299–1310 GGTCTCCCAAAT (SEQ ID NO: 30)

References

J. Sambrook, E. F. Fritsch, T. Maniatis, 'Molecular Cloning: a Laboratory Manual', Second Edition, Cold Spring Harbour Laboratory Press, 1989.

References

1. Guinosso, C. J., Hoke G. D., Freier, S. M., Martin, J. F., Ecker, D. I., Mirabelle, C. K., Crooke, S. T., Cook, P. D. Nucleosides Nucleotides (1991) 10 259–262
2. Carmo-Fonseca, M., Pepperkok, R., Sproat, B. S., Ansorge, W., Swanson, M. S., Lamond, A. I. Embo J. (1991), 7, 1863–1873
3a Cook, P. D. Anti-Cancer Drug Des. (1991) 6 585–607
b Wagner, R. W. Nature (1994) 372, 333–335
4 Uhlmann E. & Payman A, Chemical Reviews 90 (1990) 544
5 Wagner, R. W. et al Science (1993) 260 1510–1513
6 Fenster, S. D., Wagner, R. W., Froehler, B. C. & CHIN, D. J. Biochemistry (1994) 33 8391–8398
7 Chollet, A., & Kawashima, E Nucleic Acids Res (1988) 16 305–317
8 Miller, P. S., Reddy, M. P., Murakami, A., Blake, K. R., Lin, S-B., & Agris, C. H., Biochemistry (1986) 25 5092–5097
9 Letsinger R. L., Groody, E. P. Lander N., & Tanaka, T. Tetrahedron (1984) 40 137–143
10a Stein, C. A., Subasinghe, C., Shinozuka, K., & Cohen J. S. (1988) Nucleic Acids Res., 16 3209–3221
b Stec, W. J.; Gratkowski, A.; Koziolkiewicz, M.; Uznanski, B. Nucliec Acids Res., (1991)19 5883–5888
11 Marshall W. S., Caruthers, M. Science (1993) 259 1564–1570
12 Froehler, B., N G, P., Matteucci, M. Nucleic Acids Res. (1988) 16 4831–4839
13 Sood, A., Shaw, R. B., Spieluogel, B. F. J. AM. Chem. Soc. (1991) 112 9000–9007
14 Milligan, J. F., Matteucci, M. D., Martin, J. C. J. Med Chem (1993) 36(14) 1923–1937
15} Matteucci, M., Lin, K. Y., Butcher, S., Moulds, C.
16} J. Am. Chem. Soc. (1991), 113 7767 7768
17 Jones, B., Ling, K. Y., Milligan, J. F., Wadwani, S., Matteucci, M. J. Org. Chem. (1993) 58 2983–2991
18 Gait, M. J., Jones, A. S., Jones, M. D., Shepherd, M. J., Walker, R. T. J. Chem. Soc. Perkin Trans 1 (1979) 1389–1394
19 Stirchak, E. P., Summerton, J. E., Weller, D. D. J Org Chem (1987) 52 4204–4206
20 Vasseur, J. J., Debart, F., Sanghui, Y. S., Cook, P. D. J Am. Chem. Soc (1992), 114, 4006–4007
21 Debart. F., Vasseur, J. J., Sanghui, Y. S., Cook, P. D. Bioogr. Med. Chem. Lett. (1992) 2 1479–1482
22 Lieber A, Strausse M, Molecular & Cellular Biology (1995), 15
23 Field, A. K. and Goodchild, J., Exp. Opin, Invest. Drugs (1995), 4(9), 799–821

Apendix

T.N.F. Alpha Olionucleotides
SENSE Oligonucleotides
SERIES 1
(1–96 bp)
8-Oligonucleotides
  1.) CACACCCT.
  2.) GACAAGCT.
  3.) GCCAGGCA.
  4.) GGTTCTCT.
  5.) TCCTCTCA.
  6.) CATACTGA.
  7.) CCCACGGC.
  8.) TCCACCCT.
  9.) CTCTCCCC.
  10.) TGGAAAGG.
  11.) ACACCATG.
  12.) AGCACTGA.
12-Oligonucleotides
  1.) CACACCCTGACA. (SEQ ID NO:31)
  2.) AGCTGCCAGGCA. (SEQ ID NO:32)
  3.) GGTTCTCTTCCT. (SEQ ID NO:33)
  4.) CTCACATACTGA. (SEQ ID NO:34)
  5.) CCCACGGCTCCA. (SEQ ID NO:35)
  6.) CCCTCTCTCCCC. (SEQ ID NO:36)
  7.) TGGAAAGGACAC. (SEQ ID NO:37)
  8.) CATGAGCACTGA. (SEQ ID NO:38)
SERIES 2
(1225–1321 bp.)
8-Oligonucleotides
  1.) CTCTATTT.

2.) ATGTTTGC.
3.) ACTTGTGA.
4.) TTATTTAT.
5.) TATTTATT.
6.) TATTATTT.
7.) ATTTATTT.
8.) ACAGATGA.
9.) ATGTATTT.
10.) ATTTGGGA.
11.) GACCGGGG.
12.) TATCCTGG.

12-Oligonucleotides
1.) CTCTATTTATGT. (SEQ ID NO:39)
2.) TTGCACTTGTGA. (SEQ ID NO:40)
3.) TTATTTATTATT. (SEQ ID NO:41)
4.) TATTTATTATTT. (SEQ ID NO:42)
5.) ATTTATTTACAG. (SEQ ID NO:43)
6.) ATGAATGTATTT. (SEQ ID NO:44)
7.) ATTTGGGAGACC. (SEQ ID NO:45)
8.) GGGGTATCCTGG. (SEQ ID NO:46)

SERIES 3
(1489–1585 bp)

8-Oligonucleotides
1.) CTGTCACT.
2.) CATTGCTG.
3.) AGGCCTCT.
4.) GCTCCCCA.
5.) GGGAGTTG.
6.) TGTCTGTA.
7.) ATCGGCCT.
8.) ACTATTCA.
9.) GTGGCGAG.
10.) AAATAAAG.
11.) GTTGCTTA.
12.) GGAAAGAA.

12-Oligonucleotides
1.) CTGTCACTCATT. (SEQ ID NO:47)
2.) GCTGAGGCCTCT. (SEQ ID NO:48)
3.) GCTCCCCAGGGA. (SEQ ID NO:49)
4.) GTTGTGTCTGTA. (SEQ ID NO:50)
5.) ATCGGCCTACTA. (SEQ ID NO:51)
6.) TTCAGTGGCGAG. (SEQ ID NO:52)
7.) AAATAAAGGTTG. (SEQ ID NO:53)
8.) CTTAGGAAAGAA. (SEQ ID NO:54)

What is claimed is:

1. A method of identifying an antisense binding site in a target mRNA, which comprises:
   (1) an incubation step, wherein a target mRNA is incubated with an oligonucleotide library and a duplex-cutting RNAase under conditions which provide for the target mRNA to be cleaved at an antisense binding site; and
   (2) an identification step, wherein the antisense binding site from the position of the cut in the mRNA is identified; wherein
      (a) all of the oligonucleotides in the oligonucleotide library are present simultaneously in the incubation step with the target mRNA; and
      (b) the oligonucleotide library comprises a plurality of distinct chimeric oligonucleotides capable of hybridizing to mRNA to form a duplex, the nucleotide sequences of which each have a common length ranging from 7 to 20 bases, which are generated randomly or generated based on the sequence of the target mRNA, wherein substantially all the nucleotide sequences of said common length which are present as sub-sequences in the target mRNA are represented in the library, and wherein each nucleotide sequence comprises:
         (a) a recognition region comprising a sequence of nucleotides that is recognized as a substrate by a duplex cutting RNAase when hybridized to the mRNA thereby permitting cleavage of said mRNA; and
         (b) a flanking region on one or both sides of said recognition region, wherein said flanking region is distinct from said recognition region and comprises a sequence of chemically-modified nucleotides which binds to the mRNA sufficiently tightly to stabilize the duplex for cutting of the mRNA in the duplex by the duplex cutting RNAase, wherein the nucleotides constituting the flanking region are different from those constituting the recognition region, and wherein each oligonucleotide is protected against exonuclease attack.

2. A method according to claim 1, wherein the length of the nucleotide sequences present in the library ranges from 10 to 20 bases.

3. A method according to claim 1, wherein said recognition region comprises a sequence of oligonucleotides which is cleaved by RNAase H when hybridized to the mRNA.

4. A method according to claim 1, wherein the nucleotides constituting the recognition region are deoxyribonucleotides or phosphorothioate deoxyribonucleotides.

5. A method according to claim 1, wherein the recognition region comprises at least four nucleotides.

6. A method according to claim 5, wherein the recognition region comprises 5 to 10 nucleotides.

7. A method according to claim 1, wherein the chemically modified nucleotides constituting the flanking region are 2' modified in the sugar moiety.

8. A method according to claim 7, wherein the chemically-modified nucleotides are 2'-O methyl ribonucleotides or 2'-O allyl ribonucleotides.

9. A method according to claim 1, wherein the chemically-modified nucleotides constituting the flanking region comprise a modified base selected from 5-propynyl deoxyuridine, 5-propynyl deoxycytidine and 2-amino adenine analogues.

10. A method according to claim 1, wherein the chemically-modified nucleotides constituting the flanking region comprise a modified phosphate moiety selected from methyl phosphonate triester, phosphoramidate, phosphorodithirate and boranophosphate analogues.

11. A method according to claim 1, wherein the nucleotide sequences each comprise two flanking regions, one on either side of the recognition region.

12. A method according to claim 11, wherein each of the flanking regions is protected against exonuclease attack.

13. A method according to claim 12, wherein each of the flanking regions is protected by reverse T.

14. A method according to claim 1, wherein the duplex-cutting RNAase is from a cell extract.

15. A method according to claim 14, wherein the cell extract also contains the target mRNA.

16. A method according to claim 1, wherein the position of the cleavage at the antisense binding site in the mRNA is determined by isolating the cleaved mRNA and sequencing said isolated cleaved mRNA.

17. A method according to claim 16, wherein the cleaved target mRNA is amplified prior to isolation and sequencing.

18. A method according to claim 17, wherein the cleaved target mRNA is amplified by reverse transcription and polymerase chain reaction.

19. A method of producing an antisense oligonucleotide, which method comprises identifying an antisense binding site according to claim 1, and synthesizing an oligonucleotide capable of binding to the site.

* * * * *

SEQUENCE LISTING

<160> NUMBER OF SEQ ID NOS: 54

<210> SEQ ID NO 1
<211> LENGTH: 32
<212> TYPE: DNA
<213> ORGANISM: Artificial Sequence
<220> FEATURE:
<223> OTHER INFORMATION: primer

<400> SEQUENCE: 1
caucaucauc auttctgctc taaaagctgc tg          32

<210> SEQ ID NO 2
<211> LENGTH: 34
<212> TYPE: DNA
<213> ORGANISM: Artificial Sequence
<220> FEATURE:
<223> OTHER INFORMATION: primer

<400> SEQUENCE: 2
cuacuacuac uacctaagca acctttattt ctcg         34

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
gattcaggaa tgtgtggcct                         20

<210> SEQ ID NO 4
<211> LENGTH: 30
<212> TYPE: DNA
<213> ORGANISM: Artificial Sequence
<220> FEATURE:

<223> OTHER INFORMATION: primer

<400> SEQUENCE: 4
cctgggattc aggaatgtgt ggcctgcaca                                              30

<210> SEQ ID NO 5
<211> LENGTH: 23
<212> TYPE: DNA
<213> ORGANISM: Artificial Sequence
<220> FEATURE:
<223> OTHER INFORMATION: primer

<400> SEQUENCE: 5
caacctcctc ctctgccatc aag                                                    23

<210> SEQ ID NO 6
<211> LENGTH: 32
<212> TYPE: DNA
<213> ORGANISM: Artificial Sequence
<220> FEATURE:
<223> OTHER INFORMATION: primer

<400> SEQUENCE: 6
aagctcaacc tcctctctgc catcaagagc cc                                          32

<210> SEQ ID NO 7
<211> LENGTH: 22
<212> TYPE: DNA
<213> ORGANISM: Artificial Sequence
<220> FEATURE:
<223> OTHER INFORMATION: primer

<400> SEQUENCE: 7
gttcctcagc ctcttctcct tc                                                     22

<210> SEQ ID NO 8
<211> LENGTH: 32
<212> TYPE: DNA
<213> ORGANISM: Artificial Sequence
<220> FEATURE:
<223> OTHER INFORMATION: primer

<400> SEQUENCE: 8
tgcttgttcc tcagcctctt ctccttcctg at                                          32

<210> SEQ ID NO 9
<211> LENGTH: 22
<212> TYPE: DNA
<213> ORGANISM: Artificial Sequence
<220> FEATURE:
<223> OTHER INFORMATION: primer

<400> SEQUENCE: 9
gaaaacggag gctgaacaat ag                                                     22

<210> SEQ ID NO 10
<211> LENGTH: 32
<212> TYPE: DNA
<213> ORGANISM: Artificial Sequence
<220> FEATURE:
<223> OTHER INFORMATION: primer

<400> SEQUENCE: 10
tccgtgaaaa cggaggctga acaataggct gt                                          32

```
<210> SEQ ID NO 11
<211> LENGTH: 22
<212> TYPE: DNA
<213> ORGANISM: Artificial Sequence
<220> FEATURE:
<223> OTHER INFORMATION: primer

<400> SEQUENCE: 11
ctactattca gtggccgaga aa                                              22

<210> SEQ ID NO 12
<211> LENGTH: 32
<212> TYPE: DNA
<213> ORGANISM: Artificial Sequence
<220> FEATURE:
<223> OTHER INFORMATION: primer

<400> SEQUENCE: 12
tcggcctact attcagtggc cgagaaataa ag                                   32

<210> SEQ ID NO 13
<211> LENGTH: 22
<212> TYPE: DNA
<213> ORGANISM: Artificial Sequence
<220> FEATURE:
<223> OTHER INFORMATION: primer

<400> SEQUENCE: 13
gctgccaggc aggttctctt cc                                              22

<210> SEQ ID NO 14
<211> LENGTH: 21
<212> TYPE: DNA
<213> ORGANISM: Artificial Sequence
<220> FEATURE:
<223> OTHER INFORMATION: primer

<400> SEQUENCE: 14
ctgatggtgt gggtgaggag c                                               21

<210> SEQ ID NO 15
<211> LENGTH: 21
<212> TYPE: DNA
<213> ORGANISM: Artificial Sequence
<220> FEATURE:
<223> OTHER INFORMATION: primer

<400> SEQUENCE: 15
cttcaagggc caaggctgcc c                                               21

<210> SEQ ID NO 16
<211> LENGTH: 21
<212> TYPE: DNA
<213> ORGANISM: Artificial Sequence
<220> FEATURE:
<223> OTHER INFORMATION: primer

<400> SEQUENCE: 16
gctccctggt ctccagattc c                                               21

<210> SEQ ID NO 17
<211> LENGTH: 20
<212> TYPE: DNA
<213> ORGANISM: Artificial Sequence
<220> FEATURE:
<223> OTHER INFORMATION: primer
```

<400> SEQUENCE: 17
gcctacagct ttgatccctg 20

<210> SEQ ID NO 18
<211> LENGTH: 23
<212> TYPE: DNA
<213> ORGANISM: Artificial Sequence
<220> FEATURE:
<223> OTHER INFORMATION: primer

<400> SEQUENCE: 18
gcaaccttta tttctcgcca ctg 23

<210> SEQ ID NO 19
<211> LENGTH: 43
<212> TYPE: DNA
<213> ORGANISM: Artificial Sequence
<220> FEATURE:
<223> OTHER INFORMATION: primer

<400> SEQUENCE: 19
gctgccaggc aggttctctt ccgcactgaa agcatgatcc ggg 43

<210> SEQ ID NO 20
<211> LENGTH: 42
<212> TYPE: DNA
<213> ORGANISM: Artificial Sequence
<220> FEATURE:
<223> OTHER INFORMATION: primer

<400> SEQUENCE: 20
cttcaagggc caaggctgcc ccaaggtcaa cctcctctct gc 42

<210> SEQ ID NO 21
<211> LENGTH: 40
<212> TYPE: DNA
<213> ORGANISM: Artificial Sequence
<220> FEATURE:
<223> OTHER INFORMATION: primer

<400> SEQUENCE: 21
gcctacagct ttgatccctg ggacttgaga agacctcacc 40

<210> SEQ ID NO 22
<211> LENGTH: 12
<212> TYPE: DNA
<213> ORGANISM: Artificial Sequence
<220> FEATURE:
<223> OTHER INFORMATION: oligonucleotide

<400> SEQUENCE: 22
gtgtcctttc ca 12

<210> SEQ ID NO 23
<211> LENGTH: 12
<212> TYPE: DNA
<213> ORGANISM: Artificial Sequence
<220> FEATURE:
<223> OTHER INFORMATION: oligonucleotide

<400> SEQUENCE: 23
ggggagagag gg 12

<210> SEQ ID NO 24
<211> LENGTH: 12

```
<212> TYPE: DNA
<213> ORGANISM: Artificial Sequence
<220> FEATURE:
<223> OTHER INFORMATION: oligonucleotide

<400> SEQUENCE: 24
ggtctcccaa at                                                          12

<210> SEQ ID NO 25
<211> LENGTH: 12
<212> TYPE: DNA
<213> ORGANISM: Artificial Sequence
<220> FEATURE:
<223> OTHER INFORMATION: oligonucleotide

<400> SEQUENCE: 25
aaatacattc at                                                          12

<210> SEQ ID NO 26
<211> LENGTH: 12
<212> TYPE: DNA
<213> ORGANISM: Artificial Sequence
<220> FEATURE:
<223> OTHER INFORMATION: predicted antisense sequence

<400> SEQUENCE: 26
gagcgcctcc tc                                                          12

<210> SEQ ID NO 27
<211> LENGTH: 12
<212> TYPE: DNA
<213> ORGANISM: Artificial Sequence
<220> FEATURE:
<223> OTHER INFORMATION: predicted antisense sequence

<400> SEQUENCE: 27
tggcccttga ga                                                          12

<210> SEQ ID NO 28
<211> LENGTH: 12
<212> TYPE: DNA
<213> ORGANISM: Artificial Sequence
<220> FEATURE:
<223> OTHER INFORMATION: predicted antisense sequence

<400> SEQUENCE: 28
tagacaactt aa                                                          12

<210> SEQ ID NO 29
<211> LENGTH: 12
<212> TYPE: DNA
<213> ORGANISM: Artificial Sequence
<220> FEATURE:
<223> OTHER INFORMATION: oligonucleotide

<400> SEQUENCE: 29
aaatacattc at                                                          12

<210> SEQ ID NO 30
<211> LENGTH: 12
<212> TYPE: DNA
<213> ORGANISM: Artificial Sequence
<220> FEATURE:
<223> OTHER INFORMATION: oligonucleotide

<400> SEQUENCE: 30
```

```
ggtctcccaa at                                                            12

<210> SEQ ID NO 31
<211> LENGTH: 12
<212> TYPE: DNA
<213> ORGANISM: Artificial Sequence
<220> FEATURE:
<223> OTHER INFORMATION: oligonucleotide

<400> SEQUENCE: 31
cacaccctga ca                                                            12

<210> SEQ ID NO 32
<211> LENGTH: 12
<212> TYPE: DNA
<213> ORGANISM: Artificial Sequence
<220> FEATURE:
<223> OTHER INFORMATION: oligonucleotide

<400> SEQUENCE: 32
agctgccagg ca                                                            12

<210> SEQ ID NO 33
<211> LENGTH: 12
<212> TYPE: DNA
<213> ORGANISM: Artificial Sequence
<220> FEATURE:
<223> OTHER INFORMATION: oligonucleotide

<400> SEQUENCE: 33
ggttctcttc ct                                                            12

<210> SEQ ID NO 34
<211> LENGTH: 12
<212> TYPE: DNA
<213> ORGANISM: Artificial Sequence
<220> FEATURE:
<223> OTHER INFORMATION: oligonucleotide

<400> SEQUENCE: 34
ctcacatact ga                                                            12

<210> SEQ ID NO 35
<211> LENGTH: 12
<212> TYPE: DNA
<213> ORGANISM: Artificial Sequence
<220> FEATURE:
<223> OTHER INFORMATION: oligonucleotide

<400> SEQUENCE: 35
cccacggctc ca                                                            12

<210> SEQ ID NO 36
<211> LENGTH: 12
<212> TYPE: DNA
<213> ORGANISM: Artificial Sequence
<220> FEATURE:
<223> OTHER INFORMATION: oligonucleotide

<400> SEQUENCE: 36
ccctctctcc cc                                                            12

<210> SEQ ID NO 37
<211> LENGTH: 12
<212> TYPE: DNA
<213> ORGANISM: Artificial Sequence
```

```
<220> FEATURE:
<223> OTHER INFORMATION: oligonucleotide

<400> SEQUENCE: 37
tggaaaggac ac                                                            12

<210> SEQ ID NO 38
<211> LENGTH: 12
<212> TYPE: DNA
<213> ORGANISM: Artificial Sequence
<220> FEATURE:
<223> OTHER INFORMATION: oligonucleotide

<400> SEQUENCE: 38
catgagcact ga                                                            12

<210> SEQ ID NO 39
<211> LENGTH: 12
<212> TYPE: DNA
<213> ORGANISM: Artificial Sequence
<220> FEATURE:
<223> OTHER INFORMATION: oligonucleotide

<400> SEQUENCE: 39
ctctatttat gt                                                            12

<210> SEQ ID NO 40
<211> LENGTH: 12
<212> TYPE: DNA
<213> ORGANISM: Artificial Sequence
<220> FEATURE:
<223> OTHER INFORMATION: oligonucleotide

<400> SEQUENCE: 40
ttgcacttgt ga                                                            12

<210> SEQ ID NO 41
<211> LENGTH: 12
<212> TYPE: DNA
<213> ORGANISM: Artificial Sequence
<220> FEATURE:
<223> OTHER INFORMATION: oligonucleotide

<400> SEQUENCE: 41
ttatttatta tt                                                            12

<210> SEQ ID NO 42
<211> LENGTH: 12
<212> TYPE: DNA
<213> ORGANISM: Artificial Sequence
<220> FEATURE:
<223> OTHER INFORMATION: oligonucleotide

<400> SEQUENCE: 42
tatttattat tt                                                            12

<210> SEQ ID NO 43
<211> LENGTH: 12
<212> TYPE: DNA
<213> ORGANISM: Artificial Sequence
<220> FEATURE:
<223> OTHER INFORMATION: oligonucleotide

<400> SEQUENCE: 43
atttatttac ag                                                            12
```

```
<210> SEQ ID NO 44
<211> LENGTH: 11
<212> TYPE: DNA
<213> ORGANISM: Artificial Sequence
<220> FEATURE:
<223> OTHER INFORMATION: oligonucleotide

<400> SEQUENCE: 44
atgaatgtat t                                                              11

<210> SEQ ID NO 45
<211> LENGTH: 12
<212> TYPE: DNA
<213> ORGANISM: Artificial Sequence
<220> FEATURE:
<223> OTHER INFORMATION: oligonucleotide

<400> SEQUENCE: 45
atttgggaga cc                                                             12

<210> SEQ ID NO 46
<211> LENGTH: 12
<212> TYPE: DNA
<213> ORGANISM: Artificial Sequence
<220> FEATURE:
<223> OTHER INFORMATION: oligonucleotide

<400> SEQUENCE: 46
ggggtatcct gg                                                             12

<210> SEQ ID NO 47
<211> LENGTH: 12
<212> TYPE: DNA
<213> ORGANISM: Artificial Sequence
<220> FEATURE:
<223> OTHER INFORMATION: oligonucleotide

<400> SEQUENCE: 47
ctgtcactca tt                                                             12

<210> SEQ ID NO 48
<211> LENGTH: 12
<212> TYPE: DNA
<213> ORGANISM: Artificial Sequence
<220> FEATURE:
<223> OTHER INFORMATION: oligonucleotide

<400> SEQUENCE: 48
gctgaggcct ct                                                             12

<210> SEQ ID NO 49
<211> LENGTH: 12
<212> TYPE: DNA
<213> ORGANISM: Artificial Sequence
<220> FEATURE:
<223> OTHER INFORMATION: oligonucleotide

<400> SEQUENCE: 49
gctccccagg ga                                                             12

<210> SEQ ID NO 50
<211> LENGTH: 12
<212> TYPE: DNA
<213> ORGANISM: Artificial Sequence
<220> FEATURE:
<223> OTHER INFORMATION: oligonucleotide
```

```
<400> SEQUENCE: 50
gttgtgtctg ta                                                    12

<210> SEQ ID NO 51
<211> LENGTH: 12
<212> TYPE: DNA
<213> ORGANISM: Artificial Sequence
<220> FEATURE:
<223> OTHER INFORMATION: oligonucleotide

<400> SEQUENCE: 51
atcggcctac ta                                                    12

<210> SEQ ID NO 52
<211> LENGTH: 12
<212> TYPE: DNA
<213> ORGANISM: Artificial Sequence
<220> FEATURE:
<223> OTHER INFORMATION: oligonucleotide

<400> SEQUENCE: 52
ttcagtggcg ag                                                    12

<210> SEQ ID NO 53
<211> LENGTH: 12
<212> TYPE: DNA
<213> ORGANISM: Artificial Sequence
<220> FEATURE:
<223> OTHER INFORMATION: oligonucleotide

<400> SEQUENCE: 53
aaataaaggt tg                                                    12

<210> SEQ ID NO 54
<211> LENGTH: 12
<212> TYPE: DNA
<213> ORGANISM: Artificial Sequence
<220> FEATURE:
<223> OTHER INFORMATION: oligonucleotide

<400> SEQUENCE: 54
cttaggaaag aa                                                    12
```